US005571912A

United States Patent [19]
Grozinger et al.

[11] Patent Number: 5,571,912
[45] Date of Patent: Nov. 5, 1996

[54] METHOD FOR THE PREPARATION OF 5,11-DIHYDRO-6H-DIPYRIDO [3,2-B:2',3'-E][1,4]DIAZEPINES

[75] Inventors: Karl G. Grozinger, Ridgefield; Karl D. Hargrave, Brookfield; Julian Adams, Ridgefield, all of Conn.

[73] Assignee: Boehringer Ingelheim Pharmaceuticals, Inc., Ridgefield, Conn.

[21] Appl. No.: 515,093

[22] Filed: Aug. 14, 1995

Related U.S. Application Data

[63] Continuation of Ser. No. 63,592, May 18, 1993, abandoned, which is a continuation of Ser. No. 769,094, Sep. 30, 1991, abandoned, which is a continuation-in-part of Ser. No. 600,451, Oct. 19, 1990, abandoned.

[51] Int. Cl.$^6$ .......................... C07D 471/14; A61K 31/55
[52] U.S. Cl. ............................................................. 540/495
[58] Field of Search ............................................. 540/495

[56] References Cited

U.S. PATENT DOCUMENTS 5,366,922  11/1994  Hargrave et al. ........................ 540/495

OTHER PUBLICATIONS

Havlir et al. "J. Infectious Diseases" (vol. 1971) pp. 537–545 (1995).
Wei et al. "Naturre" (vol. 373) pp. 117–122 (1995).

*Primary Examiner*—Robert T. Bond
*Attorney, Agent, or Firm*—Robert P. Raymond; Alan R. Stempel; Mary-Ellen M. Devlin

[57] ABSTRACT

This invention relates to a novel method for preparing certain dipyrido-diazepines.

11 Claims, No Drawings

METHOD FOR THE PREPARATION OF 5,11-DIHYDRO-6H-DIPYRIDO [3,2-B:2',3'-E][1,4]DIAZEPINES

RELATED APPLICATIONS

This application is a continuation of U.S. application Ser. No. 063,592, filed May 18, 1993, now abandoned, which is a continuation of U.S. application Ser. No. 769,094, filed Sep. 30, 1991, now abandoned, which is a continuation-in-part of U.S. application Ser. No. 600,451, filed Oct. 19, 1990, now abandoned.

FIELD OF THE INVENTION

This invention relates to a novel method for preparing certain 5,11-dihydro-6H-dipyrido[3,2-b:2',3'- e][1,4]diazepines

BACKGROUND OF THE INVENTION

U.S. Pat. No. 5,366,972, describes novel 5,11-dihydro-6H-dipyrido[3,2-b:2',3'- e][1,4]diazepines useful in the prevention and treatment of HIV infection and methods for preparing these compounds.

SUMMARY OF THE INVENTION

Pyridobenzodiazepine compounds prepared by the novel process of this invention and from the novel intermediates described herein have the formula:

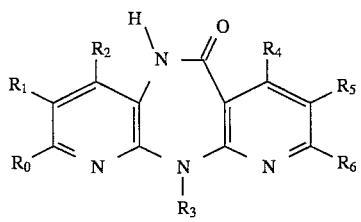

wherein $R_0$ is hydrogen or halogen;

- $R_1$ is hydrogen, alkyl of 1 to 4 carbon atoms, alkoxy or alkylthio of 1 to 4 carbon atoms, alkoxycarbonyl of 2 to 4 carbon atoms, trihalomethyl, hydroxyalkyl of 1 to 4 carbon atoms, alkanoyl of 2 to 4 carbon atoms, alkanoyloxy of 2 to 4 carbon atoms, alkanoylamino of 1 to 4 carbon atoms, aminoalkyl of 1 to 4 carbon atoms, alkoxycarbonylalkyl wherein the alkoxy and alkyl moieties each contain 1 to 2 carbon atoms, carboxyalkyl of 2 to 4 carbon atoms, mono- or di-alkylamino wherein each alkyl moiety contains 1 to 2 carbon atoms, cyano, nitro, hydroxyl, carboxyl, amino, mono- or di-alkylaminoalkyl wherein each alkyl moiety contains 1 to 2 carbon atoms, azido or halogen;
- $R_2$ is hydrogen or alkyl of 1 to 3 carbon atoms, with the proviso that if $R_1$ is other than hydrogen or alkyl of 1 to 3 carbon atoms, then $R_2$ is hydrogen;
- $R_3$ is alkyl or fluoroalkyl of 1 to 5 carbon atoms, cycloalkyl of 3 to 6 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxyalkyl of 2 to 5 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, hydroxy or halogen) or alkoxycarbonylmethyl wherein the alkoxy moiety contains 1 to 5 carbon atoms;
- one of $R_4$, $R_5$ and $R_6$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylaminoalkyl wherein each alkyl moiety contains 1 to 2 carbon atoms, halogen, cyano, nitro, azido or carboxyl, with the other two substituents being hydrogen;
- or, two of $R_4$, $R_5$ and $R_6$ are independently alkyl of 1 to 2 carbon atoms, trihalomethyl, alkyloxy or alkylthio of 1 to 2 carbon atoms, or halogen, with the remaining substituent being hydrogen;
- or $R_4$, $R_5$ and $R_6$ are each hydrogen.

Preferably, $R_0$ is hydrogen, fluoro or chloro; $R_1$ and $R_2$ are each hydrogen, methyl or ethyl; and $R_3$ is alkyl of 1 to 3 carbon atoms or cycloalkyl of 3 to 6 atoms, and $R_4$, $R_5$ and $R_6$ are each hydrogen.

More preferably, $R_0$ is hydrogen, fluoro or chloro; $R_1$ and $R_2$ are each hydrogen or methyl; $R_3$ is ethyl, propyl, or cycloalkyl of 3 to 4 carbon atoms; and $R_4$, $R_5$, and $R_6$ are each hydrogen.

The process of this invention for the preparation of the compound of formula I is outlined below:

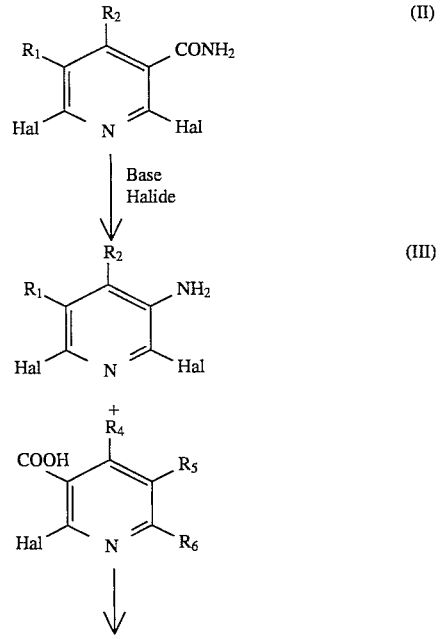

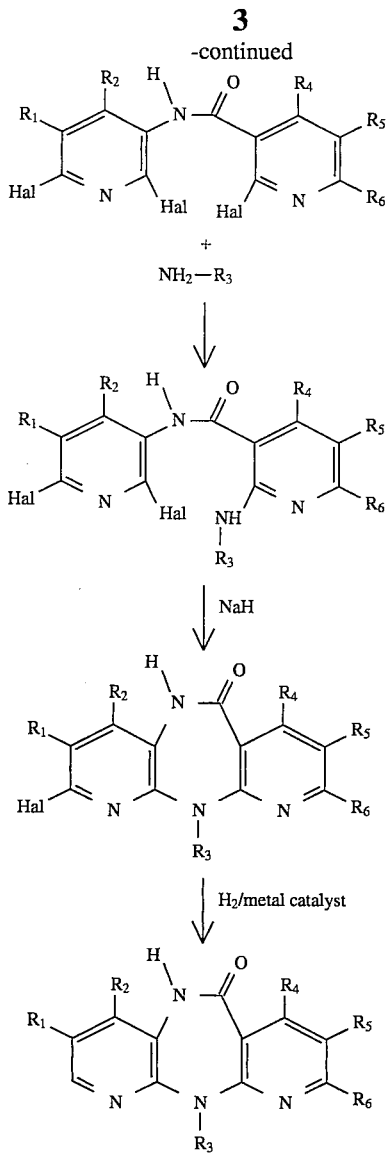

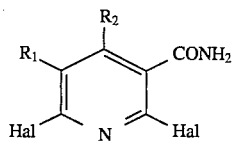

DETAILED DESCRIPTION OF THE INVENTION

The novel process of this invention for preparing the pyridobenzodiazepine of formula I comprises the following steps:

Step 1, reacting a compound having the formula (II)

wherein $R_1$ and $R_2$ are as defined above, and Hal is halogen (i.e., fluorine, chlorine, bromine or iodine), in an aqueous solution, with a base, such as NaOH, and a halide, such as bromine, chlorine or NaOBr, at temperature ranging from about 0° C. to about 100° C., to produce a compound having the formula

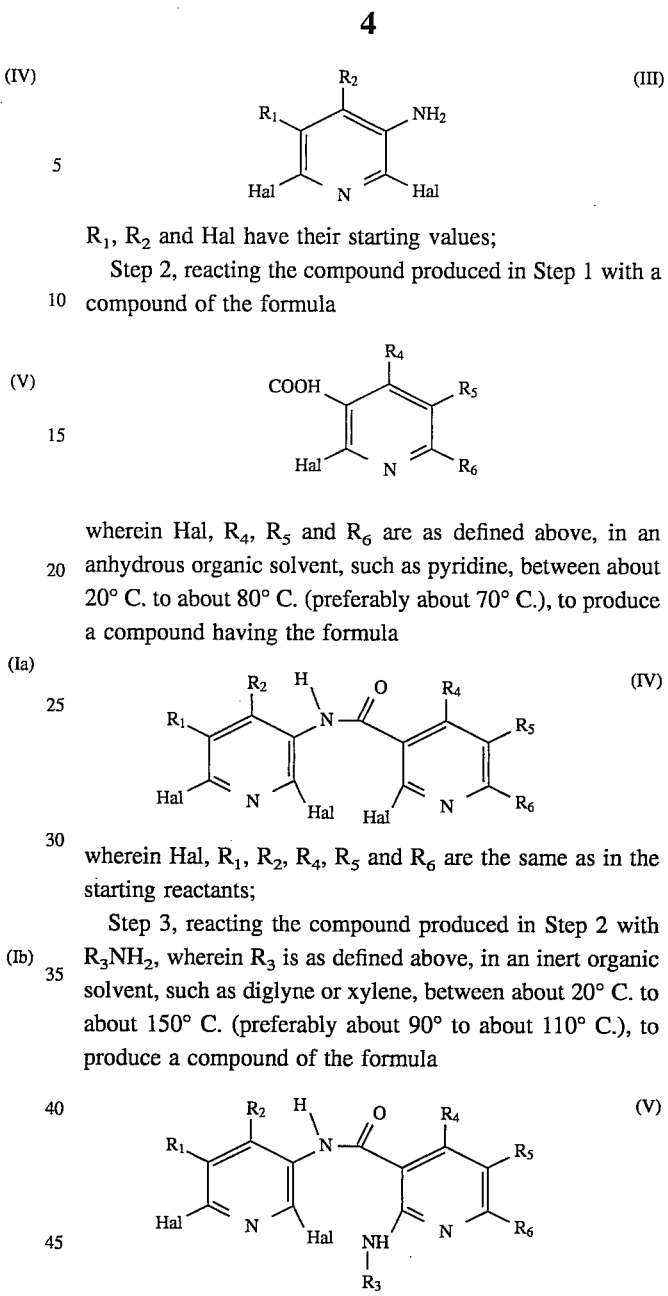

$R_1$, $R_2$ and Hal have their starting values;

Step 2, reacting the compound produced in Step 1 with a compound of the formula (V)

wherein Hal, $R_4$, $R_5$ and $R_6$ are as defined above, in an anhydrous organic solvent, such as pyridine, between about 20° C. to about 80° C. (preferably about 70° C.), to produce a compound having the formula (IV)

wherein Hal, $R_1$, $R_2$, $R_4$, $R_5$ and $R_6$ are the same as in the starting reactants;

Step 3, reacting the compound produced in Step 2 with $R_3NH_2$, wherein $R_3$ is as defined above, in an inert organic solvent, such as diglyne or xylene, between about 20° C. to about 150° C. (preferably about 90° to about 110° C.), to produce a compound of the formula (V)

wherein Hal and $R_1$–$R_6$ are the same as in the starting reactants; and

Step 4, heating the compound produced in Step 3 in an inert organic solvent, such as pyridine, DMF or diglyne, comprising sodium hydride, between about 60° C. to about 150° C.; then hydrogenating the resultant solution in the presence of a metal catalyst, such as palladium, between about 20° C. to about 100° C., to produce a mixture containing the compound of formula I; and then isolating the compound of the formula I.

Preparation A below illustrates the preparation of the 2,6-dichloro-3-pyridinecarboxamide (compound of formula II) used to prepare the dipyridodiazepinone of Example I.

Example I below illustrates the preparation of the dipyridodiazepinone of formula I wherein $R_0$, $R_1$, $R_4$, $R_5$, and $R_6$ are hydrogen, $R_2$ is methyl, and $R_3$ is cyclopropyl.

PREPARATION A

PREPARATION OF 3-CYANO-2,6-DIHYDRO-4-METHYLPYRIDINE

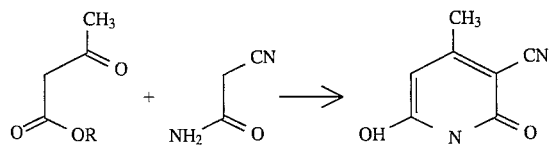

A mixture of 336g (4 moles) of cyanoacetamide, 507ml (520g, 4 moles) of ethyl acetoacetate, and 850ml of methanol was warmed to attain solution and 275g (4.18 moles) of potassium hydroxide dissolved in 220ml of methanol was added during 2 hours with stirring. During the addition a white precipitate formed and more methanol was added to prevent caking. The mixture was heated to reflux, stirred for 8 hours, cooled and filtered. The white precipitate was washed with methanol. The mono potassium salt was dissolved in warm water, filtered, cooled, acidified with concentrated hydrochloric acid, filtered, washed with water, and dried at 90° C. to yield 535g (89%).

2) PREPARATION OF 3-CYANO-2,6-DICHLORO-4-METHYLPYRIDINE

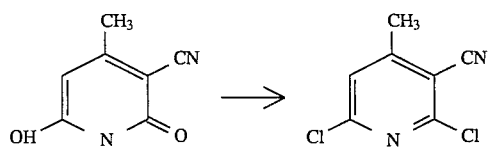

3-Cyano-2,6-dihydroxy-4-methylpyridine (50g, 0.33 mole) and phosphorous oxychloride (100ml, 1.07 mole) were placed in a glass lined stainless steel autoclave and heated to 140° C. for 8 hours. After cooling, the mixture was poured on ice and the crystalline product was filtered. The wet filter cake was dissolved in methylene chloride (100ml), dried over anhydrous $MgSO_4$, and concentrated to dryness. The material was crystallized from hot ethanol to yield 52.8g mp (102°–106° C.) (85%).

The procedure was repeated substituting phenylphosphonic dichloride (b.p.258) (3 equiv.) for phosphorous oxychloride and heating the resultant mixture at 150° C.–170° C. for 4 hours. A yield of 80%–85% of 3-cyano-2,6-dichloro-4-methylpyridine.

3. PREPARATION OF 2,6-DICHLORO-4-METHYL-3-PYRIDINECARBOXAMIDE

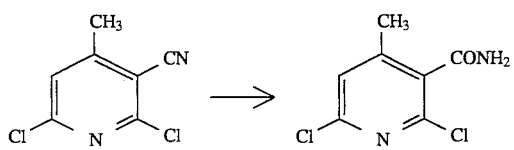

3-Cyano-2,6-dichloro-4-methylpyridine (80g, 0.42 mole) was dissolved in concentrated sulfuric acid (440ml). The mixture was heated at 150° C.–170° C. with stirring for 30 minutes, cooled and poured on ice. The precipitate was filtered and washed with water. The wet filter cake was dissolved in methylene chloride, washed, neutralized with $Na_2Co_3$, dried over $Na_2SO_4$ (anhydrous), and concentrated until a white precipitate separated. Petroleum ether was added, the crystals were filtered and dried at room temperature overnight to give 83g (94%) of 2,6-dichloro-4-methyl-3-pyridinecarboxamide.

EXAMPLE I

PREPARATION OF 11-CYCLOPROPYL-5,11-DIHYDRO-4-METHYL-6H-DIPYRIDO[3,2-b:2',3'-e][1,4]DIAZEPIN-6-ONE

A) PREPARATION OF 2,6-DICHLORO-4-METHYL-3-AMINOPYRIDINE

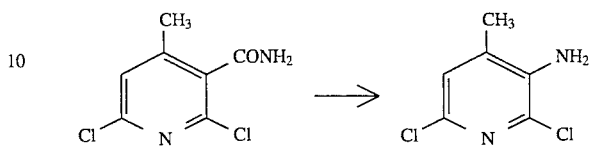

A solution of 89.2g (2.23 mole) of sodium hydroxide in 850ml of water was stirred and cooled to 0° C. in an ice/salt bath. 34.4 g (0.668 mole) of bromine was added dropwise, maintaining the temperature at 0° C. 120g (0.585 mole) of 2,6-dichloro-4-methyl-3-pyridinecarboxamide was then added at once keeping the temperature at 0° C. –5° C. The solution was slowly, over one-half hour, brought to room temperature and then heated at 70° C.–75° C. for one hour. The resulting suspension was cooled to room temperature, diluted further with 1l of water, and stirred overnight. The solid was filtered, back-washed with 1l of water, followed by 300 ml of petroleum ether and dried at 60° C. to give 89.4g (86.3%) (mp: 80° C.–83° C.) of tan crystalline 2,6-dichloro-4-methyl-3-aminopyridine.

B) PREPARATION OF 2,6-DICHLORO-3-(2'-CHLORO-3'-NICOTINYL) CARBOXAMIDO-4-METHYLPYRIDINE

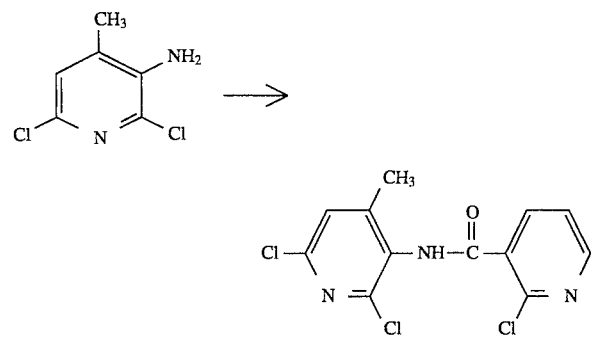

To a solution of 90.0 g (0.508 mole) of 2,5-dichloro-4-methyl-3-aminopyridine in 225ml of cyclohexane, 220ml of pyridine, and 50ml of 1,4-dioxane was added in portions over 15 minutes a solution of 100.7g (0.571 mole) of 2-chloronicotinic acid chloride in 200 ml of 1,4-dioxane. At the end of the addition, the reaction temperature reached 50° C. The mixture was stirred at room temperature for 2 days. The wet filter cake was heated at mild reflux overnight in 1l of water containing 25ml of 1N NaOH solution. (The crude product contained 8%–10% of the di-adduct, which is readily hydrolyzed in dilute sodium hydroxide solution to the required product.) The product was collected by filtration and was washed with cold water. The pure product was dried at 60° C. under vacuum to yield 60g (37.3%) (mp:168° C.–171° C.) of 2,6-dichloro-3-(2'-chloro-3'-nicotinyl) carboxamido-4-methylpyridine.

2-chloronicotinic acid chloride was prepared by refluxing 90g (0.571 mole) of 2-chloronicotinic acid in 315ml of thionylchloride for 2 hours. The excess thionylchloride was distilled off. The residue was diluted with 200ml of 1,4-dioxane and used as is.

C. PREPARATION OF 2,6-DICHLORO-3-(2'-CYCLOPROPYLAMINO-3'-NICOTINYL)CARBOXAMIDO-4-METHYLPYRIDINE

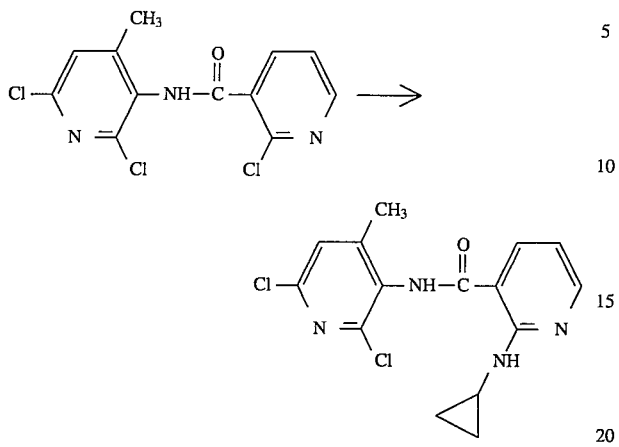

A mixture of 90g (0.284 mole) of 2,6-dichloro-3-(2'-cyclopropylamino-3'-nicotinyl) carboxamide-4-methylpyridine and 79ml (1.14 mole, 4 eq.) of cyclopropylamine in 900ml of xylene was heated in a 2l stainless steel autoclave for 2 days at 90° C.–110° C. After cooling, the xylene was concentrated to a paste and 1l of water was added. The resulting solid was filtered, back-washed with 1l of water, and 1l of petroleum ether. The product was dried at 80° C. to give 80.5g (84.1%) (mp: 163° C.–166° C.) of 2,6-dichloro-3-(2'-cyclopropylamino-3'-nicotinyl)carboxamide-4-methylpyridine.

D. PREPARATION OF 11-CYCLOPROPYL-5,11-DIHYDRO-4-METHYL-6 H-DIPYRIDO[3,2-b:2',3'-e][1,4]DIAZEPIN-6-ONE

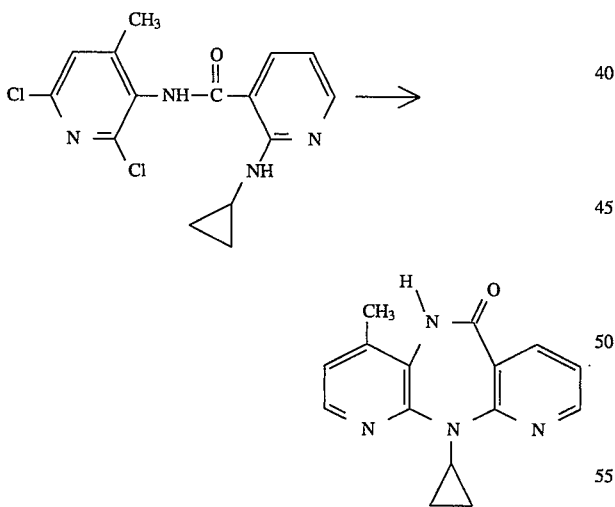

To a solution of 33g of 60% sodium hydride on mineral oil dispersion (0.825 mole of sodium hydride) in 100ml of 2-methoxyethyl ether, heated to 120° C. under nitrogen, was added dropwise over 0.5 hour 80g (0.237 mole) of 2,6-dichloro- 3-(2'-cyclopropylamino-3'-nicotinyl)carboxamide-4-methylpyridine in 400 ml of 2-methoxyethyl ether. The reaction mixture was stirred at 130° C.–135° C. for 1 hour longer, cooled to room temperature, and quenched by the careful addition of ethanol. The solution was then hydrogenated as is at 50 PSI with 8g of 10% palladium on carbon catalyst for 2 days. The catalyst was filtered and the ethanol was removed under reduced pressure. The methoxyethyl ether solution was poured into 3l of water and brought to pH7 with glacial acetic acid. The crystalline product was stirred overnight, collected and washed with pentane. The filter cake was dissolved in 500ml of hot pyridine and slow addition of 3l of water gave crystalline product. After aging overnight, the product was collected and suspended in 500 ml of isopropanol, heated to reflux, cooled and filtered. Final recrystallization from pyridiine and water gave, after drying at 100° C., 45.8g (72.5%) (mp:253° C.–254° C.) of 11-cyclopropyl-5,11-dihydro-4-methyl-6 H-dipyrido[3,2-b:2',3'-e][1,4]diazepin-6-one.

What is claimed is:

1. A method for the preparation of a compound of the formula:

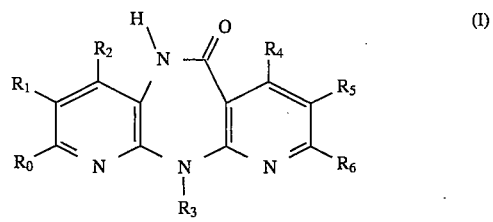

wherein $R_0$ is hydrogen or halogen;

$R_1$ is hydrogen, alkyl of 1 to 4 carbon atoms, alkoxy or alkylthio of 1 to 4 carbon atoms, alkoxycarbonyl of 2 to 4 carbon atoms, trihalomethyl, hydroxyalkyl of 1 to 4 carbon atoms, alkanoyl of 2 to 4 carbon atoms, alkanoyloxy of 2 to 4 carbon atoms, alkanoylamino of 1 to 4 carbon atoms, aminoalkyl of 1 to 4 carbon atoms, alkoxycarbonylalkyl wherein the alkoxy and alkyl moieties each contain 1 to 2 carbon atoms, carboxyalkyl of 2 to 4 carbon atoms, mono- or di-alkylamino wherein each alkyl moiety contains 1 to 2 carbon atoms, cyano, nitro, hydroxyl, carboxy, amino, mono- or di-alkylaminoalkyl wherein each alkyl moiety contains 1 to 2 carbon atoms, azido or halogen;

$R_2$ is hydrogen or alkyl of 1 to 3 carbon atoms, with the proviso that if $R_1$ is other than hydrogen or alkyl of 1 to 3 carbon atoms, then $R_2$ is hydrogen;

$R_3$ is alkyl or fluoroalkyl of 1 to 5 carbon atoms, cycloalkyl of 3 to 6 carbon atoms, alkenyl or alkynyl of 2 to 5 carbon atoms, alkoxyalkyl or alkylthioalkyl of 2 to 4 carbon atoms, alkanoyl of 2 to 4 carbon atoms, hydroxylakyl of 2 to 4 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, hydroxy or halogen), or alkoxycarbonylmethyl wherein the alkoxy moiety contains 1 to 5 carbon atoms;

one of $R_4$, $R_5$ and $R_6$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylaminoalkyl wherein each alkyl moiety contains 1 to 2 carbon atoms, halogen, cyano, nitro, azido or carboxyl, with the other two substituents being hydrogen; or, two of $R_4$, $R_5$ and $R_6$ are independently alkyl of 1 to 2 carbon atoms, trihalomethyl, alkyloxy or alkylthio of 1 to 2 carbon atoms, or halogen, with the remaining substituent being hydrogen; or $R_4$, $R_5$ and $R_6$ are each hydrogen, which method comprises the following steps:

a) reacting a compound having the formula

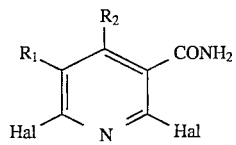

(II)

wherein Hal is halogen, and $R_1$ and $R_2$ are as defined above, with a base and a halide, in an aqueous solution, at about 0° C. to about 100° C., to produce a compound having the formula

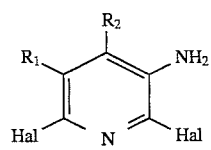

(III)

b) reacting the compound of formula III prepared in a), with a compound of the formula

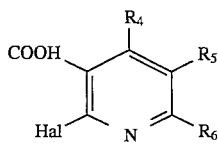

wherein Hal, $R_4$, $R_5$, and $R_6$ are as defined above, in an anhydrous organic solvent, between about 20° C. to about 80° C., to produce a compound having the formula

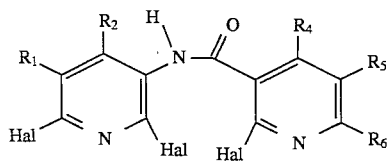

(IV)

c) reacting the compound of formula IV prepared in b), with a compound of the formula $R_3NH_2$, in an inert organic solvent at between about 20° C. to about 150° C., to produce a compound of the formula

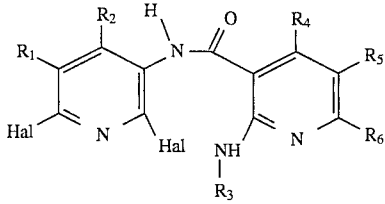

(V)

d) heating the compound of formula V prepared in c), in an inert organic solvent comprising sodium hydride at between about 60° C. to about 150° C. to produce a compound of the formula

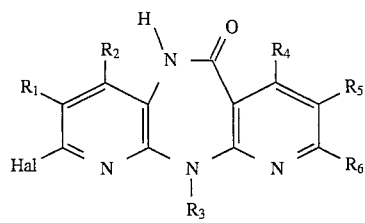

(Ia)

and, optionally, e) hydrogenating the compound of formula Ia prepared in d), in the presence of a metal catalyst, between about 20° C. to about 100° C., to produce a compound of the formula

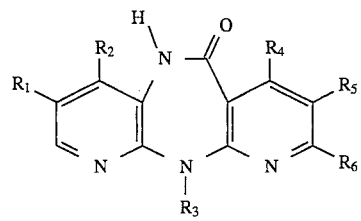

(Ib)

2. A method as recited in claim 1 wherein $R_0$ is hydrogen.
3. A method as recited in claim 1 wherein $R_0$ is halogen.
4. A method as recited in claim 1 wherein $R_0$ is hydrogen, fluoro, or chloro; and $R_1$ and $R_2$ are each hydrogen, methyl or ethyl.
5. A method as recited in claim 4 wherein $R_3$ is alkyl of 1 to 3 carbon atoms or cycloalkyl of 3 to 6 carbon atoms.
6. A method as recited in claim 5 wherein $R_4$, $R_5$ and $R_6$ are each hydrogen.
7. A method as recited in claim 4 wherein $R_3$ is ethyl, propyl, or cycloalkyl of 3 to 4 carbon atoms.
8. A method as recited in claim 5 wherein $R_1$ and $R_2$ are each hydrogen or methyl.
9. A method as recited in claim 6 wherein $R_0$ is hydrogen.
10. A method as recited in claim 6 wherein $R_0$ is fluoro or chloro.
11. A method as recited in claim 1 wherein the compound prepared is 11-cyclopropyl-5,11-dihydro-4-methyl-6H-dipyrido[3,2-b:2',3'-e][1,4]diazepin-6-one.

* * * * *